United States Patent

Edwards

(10) Patent No.: US 6,518,755 B2
(45) Date of Patent: Feb. 11, 2003

(54) MEASUREMENT TECHNIQUE AND APPARATUS FOR HIGH-RESOLUTION MULTI-VOLUME NMR WELL LOGGING

(75) Inventor: Carl M. Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/829,574

(22) Filed: Apr. 10, 2001

(65) Prior Publication Data

US 2003/0001568 A1 Jan. 2, 2003

(51) Int. Cl.$^7$ ................................................. G01V 3/00
(52) U.S. Cl. ........................................................ 324/303
(58) Field of Search ......................................... 304/303

(56) References Cited

U.S. PATENT DOCUMENTS

| | | | |
|---|---|---|---|
| 4,717,877 A | 1/1988 | Taicher et al. | 324/303 |
| 5,023,551 A | 6/1991 | Kleinberg et al. | 324/303 |
| 5,055,787 A * | 10/1991 | Kleinberg et al. | 324/303 |
| 5,055,788 A * | 10/1991 | Kleinberg et al. | 324/303 |
| 5,557,201 A | 9/1996 | Kleinberg et al. | 324/303 |
| 5,596,274 A * | 1/1997 | Sezginer | 324/303 |
| 5,796,252 A | 8/1998 | Kleinberg et al. | 324/303 |
| 5,936,405 A * | 8/1999 | Prammer et al. | 324/303 |
| 6,005,389 A | 12/1999 | Prammer | 324/303 |
| 6,018,243 A * | 1/2000 | Taicher et al. | 324/300 |
| 6,049,205 A | 4/2000 | Taicher et al. | 324/303 |
| 6,121,774 A | 9/2000 | Sun et al. | 324/303 |
| 6,163,153 A | 12/2000 | Reiderman et al. | 324/314 |
| 6,166,543 A | 12/2000 | Sezginer et al. | 324/303 |
| 6,348,792 B1 * | 2/2002 | Beard et al. | 324/300 |
| 6,445,180 B1 * | 9/2002 | Reiderman et al. | 324/303 |
| 6,452,388 B1 * | 9/2002 | Reiderman et al. | 324/303 |

FOREIGN PATENT DOCUMENTS

EP 0581666 B1 10/1997
EP 0967490 A2 12/1999

OTHER PUBLICATIONS

D. McKeon, An Improve NMR Tool Design for Faster Logging, Annual Logging Symposium, May 30, 1999, p 1–14).*

D. McKeon et al.; *An Improved NMR Tool Design for Faster Logging*, SPWLA 40th Annual Logging Symposium, May 30–Jun. 3, 1999, Paper CC, pp. 1–14, 14 Figures.

* cited by examiner

Primary Examiner—Edward Lefkowitz
Assistant Examiner—Dixomara Vargas
(74) Attorney, Agent, or Firm—Madan, Mossman & Sriram, P.C.

(57) ABSTRACT

Using phase-alternate pairs to eliminate the effects of ringing requires a large running average for multi-frequency NMR logging tools. At logging speeds greater than about five ft/min, the resolution may become unacceptable. An important realization is that field-shifting need only occur between two sensitive volumes to make sequential CPMG sequences a phase-alternate pair. Additional sensitive volumes can be obtained using the standard frequency-shifting approach. Thus, a substantial decrease in power is possible. The present invention uses a side-looking gradient NMR logging tool with 12 different sensitive volumes. An auxiliary electromagnet winding is placed so that the plane of the winding is substantially parallel to the symmetry axis of the permanent magnet configuration. The electromagnet is switched on and a CPMG sequence is performed. Immediately following this sequence the current in the electromagnet winding is reversed and a second CPMG sequence is acquired. The data from these two sequences comprise a phase-alternate pair and are combined using standard methods. The electromagnet current is sufficient to prevent the overlap of the sensitive volumes. The operating frequency of the tool can be switched and the process repeated until data from all the required sensitive volumes are acquired.

20 Claims, 4 Drawing Sheets

MEASUREMENT TECHNIQUE AND APPARATUS FOR HIGH-RESOLUTION MULTI-VOLUME NMR WELL LOGGING

BACKGROUND OF THE INVENTION

1. Field of the Invention

The present invention relates generally to a method for measuring nuclear magnetic resonance properties of an earth formation traversed by a borehole, and more particularly, to a multifrequency method for reducing the effect of any ringing, such as magnetoacoustic ringing, and DC offset, during a nuclear magnetic resonance measurement.

2. Background of the Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

A magnet on the NMR instrument is used to induce a static magnetic field in the earth formation. The static magnetic field aligns the nuclear spins of nuclei, particularly including hydrogen nuclei, in the formation in a direction parallel to that of the static field.

The NMR instrument also typically includes an antenna, positioned near the magnet and shaped so that a pulse of radio frequency (RF) power conducted through the antenna induces an RF magnetic field in the earth formation. The RF magnetic field is generally orthogonal to the field applied by the magnet. This RF pulse sometimes has a duration and amplitude predetermined so that the spin axes of the hydrogen nuclei generally align themselves perpendicularly both to the orthogonal magnetic field induced by the RF pulse and to the magnetic field applied by the magnet. After the pulse ends, the nuclear magnetic moments of the hydrogen nuclei gradually "relax" or return to their original alignment with the magnet's field. The amount of time taken for this relaxation, referred to as $T_1$, is related to petrophysical properties of interest of the earth formation.

After the pulse ends, the antenna is typically electrically connected to a receiver, which detects and measures voltages induced in the antenna by precessional rotation of the spin axes of the hydrogen nuclei. The precessional rotation generates RF energy at a frequency proportional to the strength of the magnetic field applied by the magnet, this frequency being referred to as the Larmor frequency. The constant of proportionality for the Larmor frequency is known as the gyromagnetic ratio $\gamma_0$. The gyromagnetic ratio is unique for each different chemical elemental isotope. The spin axes of the hydrogen nuclei gradually "dephase" because of inhomogeneities in the magnet's field and because of differences in the chemical and magnetic environment within the earth formation. Dephasing results in a rapid decrease in the magnitude of the voltages induced in the antenna. The rapid decrease in the induced voltage is referred to as the free induction decay (FID). The rate of FID is typically referred to by the notation $T_2^*$. The FID decay rate consists of a first component, referred to as "true $T_2$", which is due to internal nuclear environmental effects, and a second component resulting from microscopic differences in magnetic field and inhomogeneities in the earth formation. The effects of the second component can be substantially removed by a process referred to as spin-echo measurement.

One problem with analysis of NMR measurements is that the signal detected by the antenna includes a parasitic, spurious ringing that interferes with the measurement of spin-echoes. One source of the spurious signal is electromagnetic generation of ultrasonic standing waves in metal. The induced RF current within the skin depth of the metal interacts with the lattice in a static magnetic field through the Lorenz force and the coherent ultrasonic wave propagates into the metal to set up a standing wave. A reciprocal mechanism converts the acoustic energy, in the presence of the static field, to an oscillating magnetic field which is picked up by the antenna as a spurious, ringing signal.

Different types of magnetoacoustic interaction may produce a parasitic signal in the NMR antenna. Antenna wiring and other metal parts of the NMR logging tool can be affected by the static magnetic field and the RF field generated by the antenna. If the antenna is located within the strongest part of the magnet's field, when RF pulses are applied to the antenna, acoustic waves are generated in the antenna and the antenna sustains a series of damped mechanical oscillations in a process known to those skilled in the art as magnetoacoustic ringing. This ringing can induce large voltages in the antenna which are superimposed with the measurement of the voltages induced by the spin-echoes.

Another source of magnetoacoustic interaction is magnetorestrictive ringing which is typically caused when non-conductive magnetic materials, such as magnetic ferrite, are used in the antenna. If this magnetic material is located within the strong part of the RF field, application of RF pulses will generate acoustic waves in the magnet. The magnet will experience a series of damped mechanical oscillations upon cessation of the RF pulse. Magnetorestrictive ringing can also induce large voltages in the antenna which are superimposed with the measurement of the voltages induced by the spin-echoes.

One approach to reduce the effects of ringing has been to design the hardware to minimize the interaction between the electromagnetic fields and the materials in the device. For example U.S. Pat. No. 5,712,566 issued to Taicher et al. discloses a device in which the permanent magnet composed of a hard, ferrite magnet material that is formed into an annular cylinder having a circular hole parallel to the longitudinal axis of the apparatus. One or more receiver coils are arranged about the exterior surface of the magnet. An RF transmitting coil is located in the magnet hole where the static magnetic field is zero. The transmitting coil windings are formed around a soft ferrite rod. Thus, magnetoacoustic coil ringing is reduced by the configuration of the transmitting coil. Magnetorestrictive ringing of the magnet is reduced because the radial dependence of the RF field strength is relatively small due to use of the longitudinal dipole antenna with the ferrite rod. Further, magnetorestrictive ringing is reduced because the receiver coil substantially removes coupling of the receiver coil with parasitic magnetic flux due to the inverse effect of magnetostriction.

Another commonly used approach to reduce the effect of ringing is to use a so-called phase-alternated-pulse sequence. Such a sequence is often implemented as $$RFA_{\pm x}-\tau n \cdot (RFB_y-\tau-\text{echo}-\tau)-TW \quad (1)$$

where $RFA_{\pm x}$ is an A pulse, usually 90° tipping pulse and RFB is a refocusing B pulse. The ± phase of RFA is applied alternately in order to identify and eliminate systematic noises, such as ringing and DC offset through subsequent processing. By subtracting the echoes in the − sequence from the pulses in the adjoining + sequence, the ringing due to the 180° is suppressed.

The minimum acquisition time for a phase-alternated pair (PAP) is the sum of two CPMG sequence times and the wait time between the two sequences. For a CPMG sequence, the RFB pulse is a 180° pulse. Typically, the wait time is about three times the maximum spin-lattice relaxation time ($T_1$) of interest. The length of the CPMG sequence (AT) is typically of the order of the maximum transverse relaxation time ($T_2$). Because there are significant static field gradients associated with NMR logging tools, the CPMG sequence is usually much shorter than the wait time. The minimum acquisition time $T_{PAP}$ for a PAP is approximately given by $$T_{PAP}=AT+TW \equiv TR \approx AT+3T_1|_{max} \approx 3T_1|_{max} \quad (2)$$

In wireline applications, the tool moves at a vertical speed of $V_L$. As a result of the tool motion, the minimum vertical resolution $R_v$ of a moving tool is given by $$R_v|_{min} \approx A+V_L T_{PAP} \quad (3)$$

where A is the antenna aperture length. The best resolution can be obtained only when the fluids in the formation relax quickly or when the logging speed is small. In actual operation, a single PAP does not have sufficient signal-to-noise ratio (SNR) to be useful and more than one PAP is required: this further degrades the resolution.

Multi-volume tools have an advantage over single volume tools because they can fill the wait time between halves of a PAP with acquisitions for other sensitive volumes. The operation of multi-volume tools is best understood by reference to FIG. 1.

FIG. 1 shows a graph of the amplitude of the static magnetic field, with respect to distance from the magnet, for a well logging apparatus that has a gradient magnetic field. The amplitude of the static magnetic field generally decreases with respect to the lateral distance from the magnet. As is well known in the art, nuclear magnetic resonance conditions occur when a radio frequency magnetic field is applied to materials polarized along a static magnetic field where the frequency of the RF magnetic field matches the product of the static magnetic field strength and the gyromagnetic ratio of the nuclei being polarized by the static magnetic field, this product being referred to as the Larmor frequency. As can be inferred from the graph in FIG. 1, by adjusting the frequency of the RF magnetic field, the distance from the magnet at which nuclear magnetic resonance conditions occur can be changed corresponding to the static magnetic field amplitude at that particular distance from the magnet. For example, if frequency $f_1$ is the highest frequency, resonance will occur at the smallest distance to the magnet, and so on through lower frequencies $f_2$ through $f_N$. Because nuclear magnetic resonance only occurs where the static magnetic field strength matches the RF magnetic field frequency, nuclear magnetic resonance measurements can be conducted within a number of different non-overlapping sensitive volumes by inducing nuclear magnetic resonance at different frequencies. An example of a gradient tool is described in U.S. Pat. No. 5,712,566 to Taicher et al. The Taicher '566 device gives non-overlapping sensitive volumes comprising thin annular cylinders each having an average radius corresponding to the particular static magnetic field amplitude in which nuclear magnetic resonance would occur at a particular RF magnetic field frequency. The thickness of each annular cylinder would be related to the bandwidth of a receiver circuit in the NMR instrument and the rate at which the static magnetic field changes in amplitude.

Examples of multi-volume PAPs are given, for example, in U.S. Pat. No. 6,049,205 to Taicher et al, the contents of which are fully incorporated herein by reference. While multi-volume PAPs measurements are more efficient at power utilization, the resolution is still controlled by $T_{PAP}$. This is best understood by reference to FIG. 2. Shown in FIG. 2 is an example of the acquisition of six PAP sequences for six different volumes and six corresponding frequencies. The abscissa is the time in milliseconds. The acquisition sequence is indicated with the six different volumes separated. As an example, pulse sequence denoted by 101a acquires data at from a volume $V_1$ at a frequency $f_1$. This is then followed by the pulse sequences denoted by 103a for a volume $V_2$ at a frequency $f_2$, 105a for a volume $V_2$ at a frequency $f_2$, through 111a for a volume $V_6$ at a frequency $f_6$. This comprises a first half of a PAP sequence for six volumes. The phase of the RF signal is then reversed and the sequence of pulses 101b. 103b, 105b, 107b, 109b and 111b are acquired for the same sequence of six volumes $V_1, V_2 \ldots V_6$ at frequencies $f_1, f_2 \ldots f_6$. The wait time $T_w$ between the two halves of a PAP sequence for a particular volume is 4.5 seconds and is the same for all volumes. In the example shown, the acquisition time AT for each CPMG sequence is the same (0.8 seconds). Those versed in the art would recognize that each individual component of a PAP pair must occur at the same frequency because the ringing characteristics depend upon the frequency; attempting to combine CPMG sequences at different frequencies will results in incomplete subtraction of the ringing signal.

The resolution of the measurement can be calculated from number of CPMG sequences NA needed to reach a SNR threshold, the number of volumes $N_v$, and $T_{PAP}$. It is given by $$R_v = A + V_L \left(1 + \frac{NA/2-1}{N_v}\right) T_{PAP}. \quad (4)$$

The need for PAPs requires that NA be a multiple of two. The resolution is proportional to the inverse of the number of volumes. The minimum resolution from eq. (4) is for NA=2 and is the same as that given by eq. (3) regardless of the number of volumes and frequencies. Thus, using multiple volumes with corresponding frequencies may improve the power utilization, but it does not improve the resolution of an NMR logging tool.

It would be desirable to have a method of NMR data acquisition that is able to suppress ringing while improving the power efficiency of a single frequency CPMG sequence. The present invention satisfies this need.

SUMMARY OF THE INVENTION

The present invention is a method for determining a parameter of interest of an earth formation with a gradient Nuclear Magnetic Resonance (NMR)tool conveyed in a borehole. A static magnetic field is produced within a first region in the formation, preferably using a permanent magnet. NMR spin-echo signals from the first region by using a transmitter on the tool with a first pulsed radio frequency (RF) signal having a Larmor frequency corresponding to the field strength in the first region as the first half of a phase alternated pair (PAP) of measurements. An electromagnet on the tool is used to alter the static field to alter the static field so that the altered static field has the same field strength (and Larmor frequency) in a second region of the formation that is non-overlapping with the first region and the second half of the PAP is obtained. The combination of the two echo sequences can reduce the effects of ringing. This may be repeated for additional regions with different Larmor frequencies. Due to the non-overlapping of the two regions, depending upon the number of repetitions needed to obtain adequate signal to noise ratio, the total acquisition time using field and frequency shifting may be significantly less that for prior art methods that only use frequency shifting.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein.

DETAILED DESCRIPTION OF PREFERRED EMBODIMENTS

Figure 3:
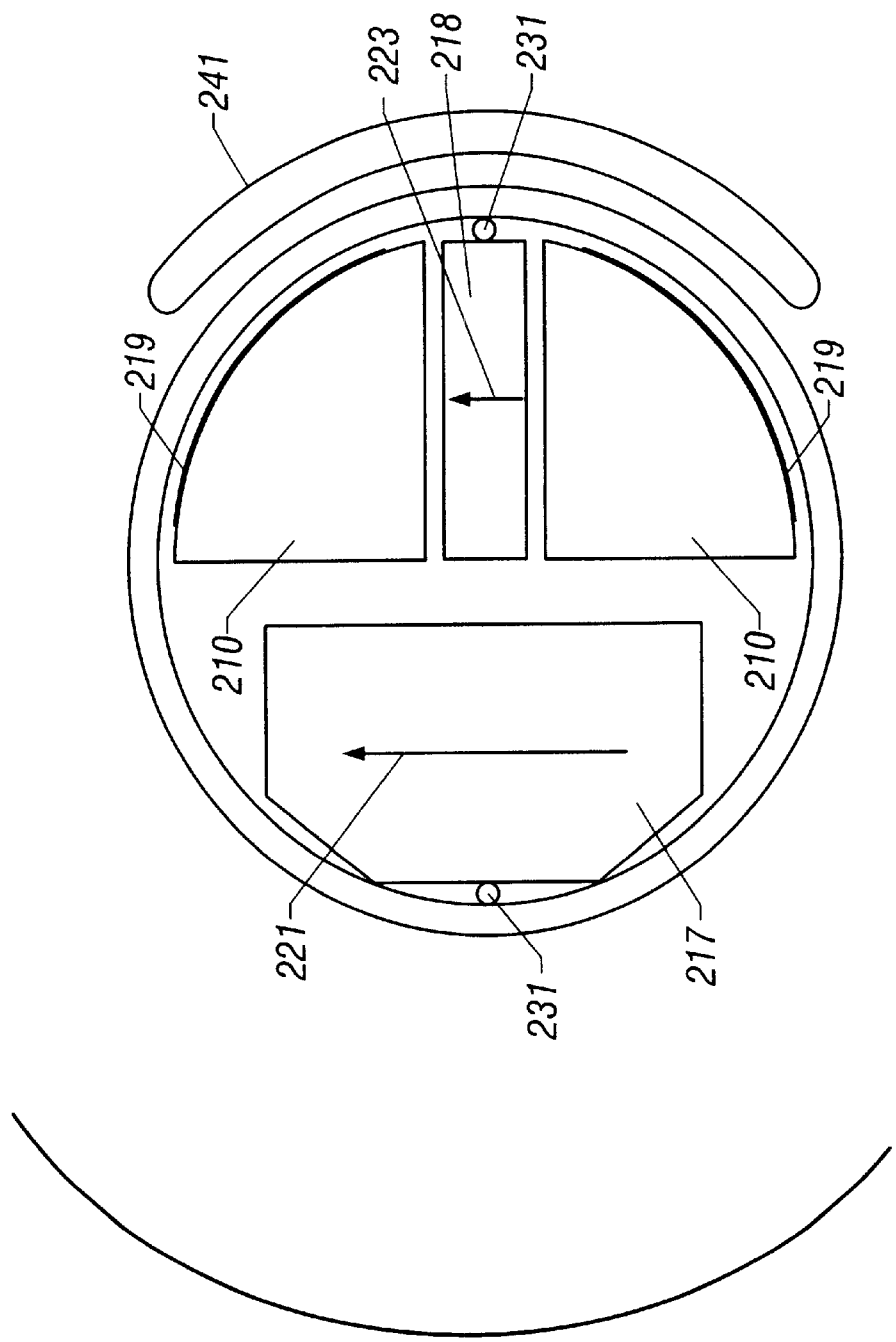
FIG. 3 is a schematic diagram of a side-looking NMR tool suitable for use with the method of the present invention.

FIG. 3 schematically illustrates an apparatus suitable for preferred embodiment of the present invention wherein this shaping of the static and RF fields is accomplished. This is a modification of a tool described in co-pending U.S. patent application Ser. No. 09/677,359 of Reiderman et al and having the same assignee as the present application. The tool cross-sectional view in FIG. 3 illustrates a main magnet 217, a second magnet 218, and a transceiver antenna, comprising wires 219 and core material 210. The arrows 221 and 223 depict the polarization (i.e., from the South pole to the North pole) of the main magnet 217 and the secondary magnet 218. A noteworthy feature of the arrangement shown in FIG. 3 is that the region of examination is towards the side of the tool rather than towards the front of the tool as in prior art devices. This region of investigation is generally indicated by the arcuate zone 241. An electromagnet with coils indicated by 231 is used to alter the static magnetic field and thus move the region of examination closer to or away from the tool.

Figure 1:
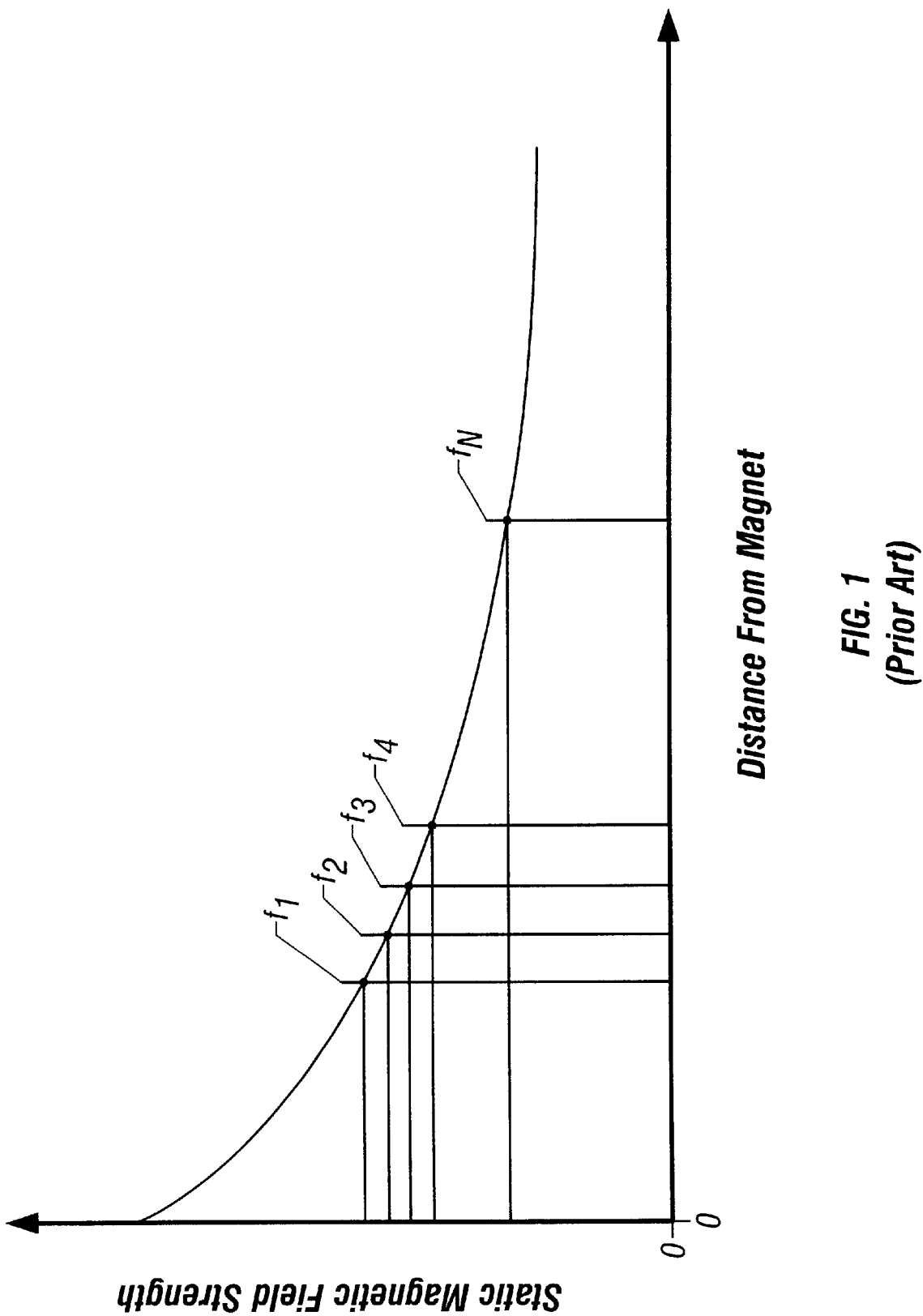
FIG. 1 (PRIOR ART) shows a graph of amplitude of the static magnetic field of the magnet in a gradient NMR well logging apparatus used with the invention.
Figure 2:
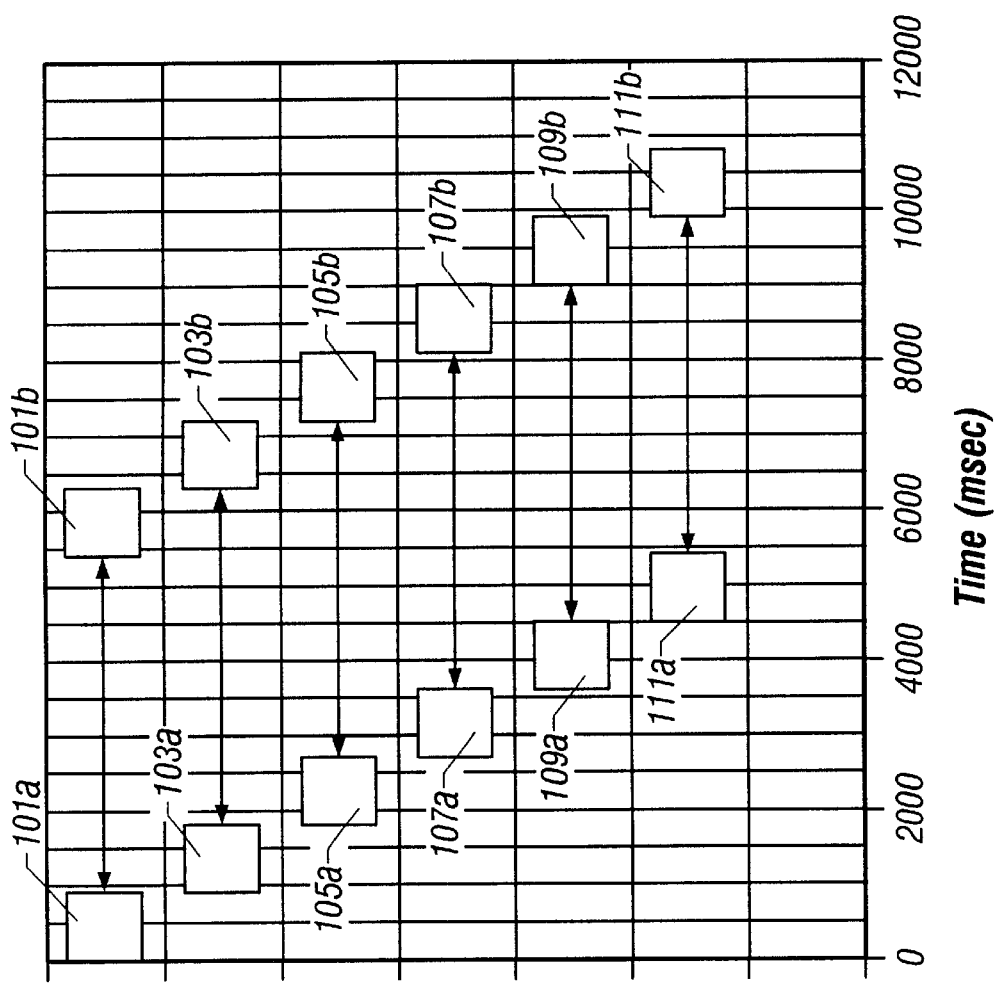
FIG. 2 (PRIOR ART) shows the timing of a multi-volume CPMG sequence for use with a gradient logging tool.
Figure 4:
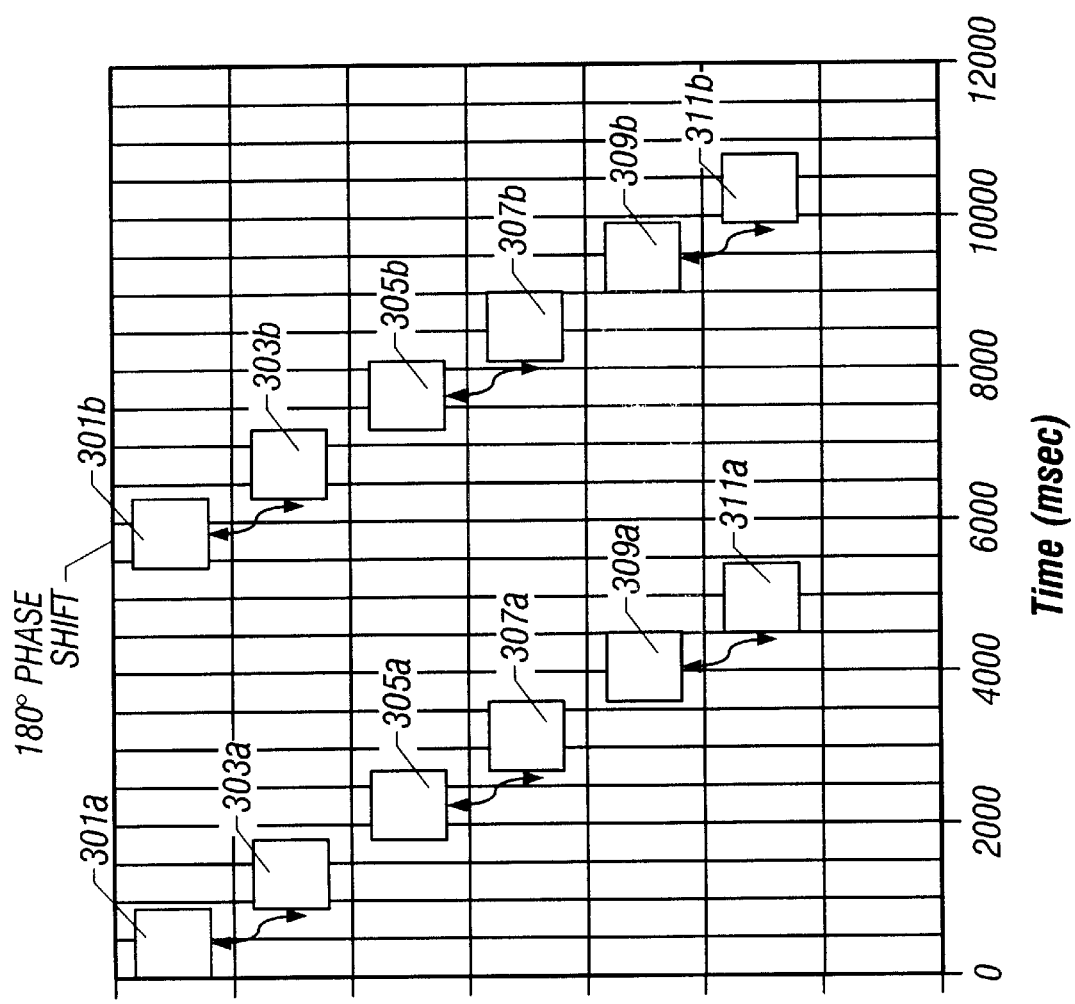
FIG. 4 shows the timing of a multi-volume CPMG sequence of the present invention for use with a gradient logging tool.

Turning now to FIG. 4, an example of the pulse sequence of the present invention for acquisition in six volumes is shown. At first sight, this appears to be identical to the prior art method shown in FIG. 2. The similarity is deceptive as will be clear from the following discussion.

Data are first acquired using a pulse sequence denoted by 301a for a first volume $V_1$ at a frequency $f_1$. This then followed by the pulses sequence 303a for a second volume $V_2$. However, the frequency for the second volume $V_2$ is unchanged, i.e., it is still $f_1$. This change of volume is accomplished by activating the electromagnet 231 described with reference to FIG. 3. Thus, the pair of sequences 301a, 303a comprise a PAPs. The total acquisition time for this PAPs is much shorter than the time interval for a PAPs such as 101a, 101b in FIG. 2. The electromagnet is turned off and another PAPs 305a, 307a is acquired at a different frequency $f_2$. This is followed by an additional PAPs 309a, 311a at frequency $f_3$ giving a total of six different volumes at three different frequencies.

The sequence of PAPs for six different volumes for three frequencies is then repeated for PAPs (301b, 303b), (305b, 307b) and (309b, 311b). The resolution for the embodiment shown in FIG. 4 is given by $$R_v = A + V_L(NA-1)T_{PAP} \quad (5)$$

where $$T_{PAP} = TR/N_v \approx 3T_1/N_v \quad (6)$$

Table 1 shows a comparison of the resolution obtained with the present invention (FIG. 4) with a prior art method (FIG. 2) for measurement in six volumes for values of TR=5400 ms. and AT=900 ms.

TABLE I

Comparison of resolution of present method with prior art

| NA | VL | RES | |
|---|---|---|---|
| | | Frequency shifted | Field and freq. shifted |
| 2 | 16.7 | 3.5 | 2.2 |
| 4 | 16.7 | 3.7 | 2.7 |
| 12 | 16.7 | 2.7 | 4.7 |
| 2 | 8.3 | 3.3 | 2.1 |
| 4 | 8.3 | 2.5 | 2.3 |
| 12 | 8.3 | 2.9 | 3.3 |

The best resolution of the measurement at $V_L$=17 ft/min is 3.5 ft. for the frequency-shifted example (prior art) and 2.3 ft. for the field/frequency shifted acquisition (present method). To obtain the same resolution as this example of the invention, the frequency-shifted example would have to be logged at 2.8 ft/min. If more data averaging is required to reach the threshold SNR, the difference is smaller. For a running average of four, the frequency shifted acquisition would need to be logged at 7.1 ft/min as compared to 17 ft/min. However, this is still a significant difference. As long as NA<2$N_v$, the present method gives improved resolution. As long as the electromagnet is powerful enough to shift the field sufficiently so that the two halves of a PAPs come from non-overlapping volumes, the present invention may be used.

There are commonly encountered logging situations, such as those encountered in a gas reservoir, where at least twelve data volumes may be required for obtaining the desired resolution of the $T_2$ spectra, the improvement in resolution by using the present invention is even more dramatic.

The present invention of field and frequency shifting can be used with a variety of logging tools, not just a side-looking NMR tool as described above. The addition of an electromagnet to most NMR logging tool designs is possible. The only requirement is that the field produced by the electromagnet is of sufficient strength to completely separate one sensitive volume from another. In practice, this is possible only with tool designs that have well defined sufficiently large gradients at the sensitive volume.

U.S. Pat. No. 5,796,252 to Kleinberg et al., the contents of which are fully incorporated herein by reference, discloses a side-looking NMR tool. In this patent, Kleinberg describes an NMR tool with the capability of changing the static magnetic field gradient during the measurement of formation properties. The change is caused by switching the electric current in an electromagnet. One of the novel features is that the electromagnet is an integral part of the RF antenna. Thus both DC and RF currents flow in the antenna. The device of the Kleinberg '252 patent may be used with the method of the present invention.

U.S. Pat. No. 4,717,877 to Taicher et al, the contents of which are fully incorporated herein by references, discloses a centralized tool for making NMR measurements. The tool includes an elongated magnet for producing a static magnetic field in the formation. It discloses the use of an electromagnet to scan through a number of sensitive volumes. It also discloses changing the tool operating frequency for the same purpose, as well as a combination of the two techniques. The purpose disclosed for doing this is to produce a radial image of the formation properties. The device used in the Taicher '877 patent may also be used with the method of the present invention.

U.S. Pat. No. 5,557,201 to Kleinberg et al describes an opposed-pole configuration for NMR logging while drilling. In order to cancel unwanted signal from drilling fluids, an electromagnet is provided. Its purpose is to produce a strong magnetic field in the borehole and a weak magnetic field in the formation. By doing this the unwanted signal can be eliminated. This electromagnet is not intended to change location of the sensitive volume, but instead eliminates signals from undesired volumes. However, the device disclosed therein is also suitable for use with the method of the present invention.

Centralized tool designs may require the electromagnet to dissipate large amounts of power to produce the required field. The power requirements for a side-looking design are much smaller; consequently, the method of the present invention is preferably used with a side-looking tool for providing the pulse sequences.

The invention has been described above using a CPMG pulse sequence for obtaining pulse echo signals. An alternate embodiment of the invention uses the pulse sequence described in U.S. Pat. No. 6,163,153 to Reiderman et al for reducing power consumption wherein the RFB pulses in eq. (1) have a tipping angle of less than the 180° associated with the CPMG sequence.

The invention has further been described by reference to logging tools that are intended to be conveyed on a wireline. However, the method of the present invention may also be used with measurement-while-drilling (MWD) tools, or logging while drilling (LWD) tools, either of which may be conveyed on a drillstring or on coiled tubing. While logging speed is usually not a factor that affects the resolution obtainable in MWD or LWD applications, tool vibration is a problem and it is desirable to obtain a PAPs within as short a time as possible. For such applications, the method of the present invention is useful in that the two halves of a PAP sequence can be obtained within a period when the tool motion is minimal.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method for determining a parameter of interest of an earth formation with a gradient Nuclear Magnetic Resonance (NMR) tool conveyed in a borehole within the formation, the method comprising:

(a) producing a static magnetic field having a first field strength in a first region in the formation;

(b) obtaining a first set of NMR spin-echo signals from said first region by activating a transmitter on the tool with a first pulsed radio frequency (RF) signal having a first frequency corresponding to said first field strength;

(c) using a magnet on the tool for producing an altered static field having said first field strength in a second region substantially non-overlapping with said first region;

(d) activating a transmitter on the tool with a second pulsed RF signal at said first frequency and obtaining a second set of NMR spin-echo signals, said second pulsed RF signal having a phase shifted 180° from a phase of the first pulsed RF signal; and (e) combining the first and second set of spin-echo signals to obtain the parameter of interest.

2. The method of claim 1 wherein the first field has a gradient in the at least one first and second regions.

3. The method of claim 1 wherein activating said transmitter produces a RF field having a direction substantially orthogonal to a direction of the static field in the at least one first and second regions.

4. The method of claim 1 wherein producing said static magnetic field further comprises using a permanent magnet.

5. The method of claim 1 wherein altering said the static field further comprises using an electromagnet.

6. The method of claim 5 wherein producing said altered static field further comprises selecting said electromagnet to be of sufficient strength to provide said condition of substantial non-overlap between the first and second regions.

7. The method of claim 1 further comprising repeating steps (a)–(e) ($N_v/2-1$) times to obtain data from a number $N_v$ of substantially non-overlapping first and second regions.

8. The method of claim 1 wherein the first and second pulsed RF signals each comprise a number NA of CPMG sequences.

9. The method of claim 1 wherein the first and second pulsed RF signals each comprise a number NA of modified CPMG sequence having refocusing pulses having a tipping angle between 90° and 180°.

10. The method of claim 7 wherein the first and second pulsed RF signals each comprise a number NA of CPMG sequences and wherein NA is greater than or equal to two times $N_v$.

11. The method of claim 7 wherein the first and second pulsed RF signals each comprise a number NA of modified CPMG sequence having refocusing pulses having a tipping angle between 90° and 180°.

12. The method of claim 1 wherein said logging tool is conveyed on one of (i) a wireline, (ii) a drillstring, and, (iii) coiled tubing.

13. The method of claim 7 wherein said earth formation comprises a gas reservoir and wherein $N_v$ is greater than 10.

14. The method of claim 1 wherein said NMR tool is a side-looking tool.

15. The method of claim 1 wherein said NMR tool is a centralized tool.

16. The method of claim 1 further comprising moving the tool along an axial direction of the borehole in a time interval between activating said transmitter with the first and second RF signal.

17. The method of claim 1 wherein said NMR tool is conveyed on one of: (i) a wireline, (ii) a drillstring, and, (iii) coiled tubing.

18. The method of claim 1 wherein said NMR tool is part of a measurement-while-drilling (MWD) apparatus, and wherein said first and second set of spin-echo signals are obtained when a radial motion of the apparatus is below a predetermined threshold.

19. A method for determining a parameter of interest of an earth formation with a gradient Nuclear Magnetic Resonance (NMR) tool conveyed in a borehole within the formation, the method comprising:
   (a) using a magnet on the tool, said tool at a first axial position in the borehole, for producing a static magnetic field having a first field strength in a first region in the formation at a first radial distance from an axis of the borehole;
   (b) obtaining a first set of NMR spin-echo signals from said first region by activating a transmitter on the tool with a first pulsed radio frequency (RF) signal having a first frequency corresponding to said first field strength;
   (c) moving the tool to a second axial position in the borehole and using an electromagnet on the tool for producing an altered static field having said first field strength in a second region at a second distance from said axis of the borehole, said second region substantially non-overlapping with said first region;
   (d) at the second axial position of the tool activating a transmitter thereon with a second pulsed RF signal at said first frequency and obtaining a second set of NMR spin-echo signals, said second pulsed RF signal having a phase shifted 180° from a phase of the first pulsed RF signal; and
   (e) combining the first and second set of spin-echo signals to obtain the parameter of interest.

20. A Nuclear Magnetic Resonance (NMR) sensing apparatus comprising:
   (a) at least one primary magnet to generate a static magnetic field in a volume containing materials sought to be analyzed, said at least one primary magnet having a longitudinal axis and being magnetized in a magnetization direction substantially perpendicular to said longitudinal axis, said magnetic field of said first magnet substantially that of an equivalent dipole magnet;
   (b) a radio frequency (RF) antenna for inducing a RF magnetic field in said volume and exciting nuclei therein and receiving signals from said excited nuclei, said RF magnetic field substantially that of a RF dipole orthogonal to the equivalent dipole magnet and displaced laterally therefrom;
   (c) a second magnet having a magnetization substantially parallel to the magnetization of the at least one primary magnet, said second magnet disposed from the at least one primary magnet and the RF antenna for shaping said static magnetic field thereby defining a first arcuate region of investigation in said volume wherein said static magnetic field has a field strength within predetermined limits and wherein said RF magnetic field has a substantially uniform field strength and is substantially orthogonal to the shaped static magnetic field; and
   (d) an electromagnet for altering the static field and defining a second arcuate region of investigation in said volume wherein said static magnetic field has a field strength within said predetermined limits;
   wherein said first and second arcuate regions are substantially non-overlapping.

* * * * *